(12) United States Patent
Kayane et al.

(10) Patent No.: US 6,475,470 B1
(45) Date of Patent: Nov. 5, 2002

(54) COMPOSITIONS FOR ORAL CAVITY

(75) Inventors: Shigeto Kayane, Tokyo (JP); Yoshitaka Yanou, Tokyo (JP); Hidetake Fujinaka, Tokyo (JP); Hidenori Yoshida, Tokyo (JP); Yoshinori Murakami, Tokyo (JP); Akira Suzuki, Tokyo (JP); Koji Maeda, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/787,408

(22) PCT Filed: Sep. 10, 1999

(86) PCT No.: PCT/JP99/04935

§ 371 (c)(1),
(2), (4) Date: Mar. 21, 2001

(87) PCT Pub. No.: WO00/18364

PCT Pub. Date: Apr. 6, 2000

(30) Foreign Application Priority Data

Sep. 25, 1998  (JP) ............................................. 10-271721
Dec. 21, 1998  (JP) .......................................... 10-362263

(51) Int. Cl.$^7$ ................................................. A61K 7/16
(52) U.S. Cl. ........................................................ 424/49
(58) Field of Search ..................................... 424/49–58

(56) References Cited

U.S. PATENT DOCUMENTS

| | | | | |
|---|---|---|---|---|
| 3,250,686 A | * | 5/1966 | Menkart et al. ............... | 167/85 |
| 3,574,824 A | * | 4/1971 | Echeandia et al. ............ | 424/50 |
| 4,132,771 A | * | 1/1979 | Schreiber et al. ............. | 424/52 |
| 4,159,316 A | * | 6/1979 | Januszewski et al. ......... | 424/49 |
| 4,187,287 A | * | 2/1980 | Schreiber et al. ............. | 424/49 |
| 4,582,701 A | * | 4/1986 | Piechota et al. ............... | 424/52 |
| 4,626,550 A | * | 12/1986 | Hertzenborg ................. | 514/770 |
| 4,627,972 A | * | 12/1986 | Gioffre et al. ................. | 424/44 |
| 4,647,451 A | * | 3/1987 | Piechota et al. ............... | 424/52 |
| 4,812,306 A | * | 3/1989 | Cocherell et al. ............. | 424/52 |
| 4,818,518 A | * | 4/1989 | Gioffre et al. ................. | 424/44 |
| 4,894,232 A | | 1/1990 | Reiil et al. | |
| 4,983,385 A | | 1/1991 | Hasegawa et al. | |
| 5,496,541 A | | 3/1996 | Cutler et al. | |
| 5,747,004 A | * | 5/1998 | Giani et al. ................... | 424/49 |
| 5,882,630 A | * | 3/1999 | Gates et al. ................... | 424/49 |
| 6,048,913 A | | 4/2000 | Yamagishi et al. | |

FOREIGN PATENT DOCUMENTS

| | | |
|---|---|---|
| EP | 0 306 454 A2 | 3/1989 |
| EP | 0 643 963 A2 | 3/1995 |
| EP | 0 728 477 A2 | 8/1996 |
| JP | 02196717 A2 * | 8/1990 |
| JP | 06256168 A * | 9/1994 |
| JP | 06287133 A * | 10/1994 |
| WO | 9749374 * | 12/1997 |

OTHER PUBLICATIONS

Abstract (XP002184560), Database WPI, Section Ch, Week 198235, Derwent Publications Ltd., London, GB; Class A96, AN 1982–73233E.
Abstract (XP002184561), Database WPI, Section Ch, Week 198139, Derwent Publications Ltd., London, GB; Class A96, AN 1981–70773D.

* cited by examiner

*Primary Examiner*—Shep K. Rose
(74) *Attorney, Agent, or Firm*—Oblon, Spivak, McClelland, Maier & Neustadt, P.C.

(57) ABSTRACT

This invention relates to compositions for the oral cavity, each of which comprises (A) a pharmaceutically-active agent, which acts on the periodontium, or a microbicidal agent and (B) an exothermic ingredient or a water-soluble high-molecular substance, and has a water content not higher than 5 wt. %. They permit adsorption of a pharmaceutically-active agent or the like at a high rate on the oral mucosas and are excellent in the effects of preventing and/or treating paradental diseases.

15 Claims, 1 Drawing Sheet

COMPOSITIONS FOR ORAL CAVITY

This application is a 371 of PCT/JP99/04935 filed Sep. 9, 1999.

TECHNICAL FIELD

This invention relates to compositions for the oral cavity, which permit adsorption of a pharmaceutically-active agent or a microbicidal agent at a high rate on the oral mucosas and are excellent in the effects of preventing and/or treating paradental diseases.

BACKGROUND ART

A variety of pharmaceutically-active agents is added in a composition for the oral cavity to prevent and/or treat paradental diseases. The pharmaceutically-active agents so added are desired to be adsorbed on the oral mucosas and to act effectively. Upon rinsing, however, their pharmaceutically-active ingredients are washed away so that not many of them are adsorbed on the mucosas. Further, no sufficient effects were available for the prevention and/or treatment of paradental diseases.

An object of the present invention is to provide a composition for the oral cavity, which permits adsorption of a pharmaceutically-active agent or a microbicidal agent at a high rate on the oral mucosas and is excellent in the effects of preventing and/or treating paradental diseases.

DISCLOSURE OF THE INVENTION

The present inventors have found that, when a pharmaceutically-active agent or a microbicidal agent and an exothermic ingredient or a water-soluble high-molecular substance are combined and the water content of the resulting composition for the oral cavity is controlled not higher than 5 wt.%, the adsorption rate of the added pharmaceutically-active agent or microbicidal agent on the oral mocosas becomes higher, thereby bringing about excellent effects for the prevention and/or treatment of paradental diseases.

Accordingly, the present invention provides a composition for the oral cavity, comprising (A) a pharmaceutically-active agent, which acts on the periodontium, or a microbicidal agent and (B) an exothermic ingredient or a water-soluble high-molecular substance, said composition having a water content not higher than 5 wt.%.

The present invention also provides an intraoral treatment method, which comprises brushing the teeth and/or gingivae with the above-described composition for the oral cavity.

BEST MODES FOR CARRYING OUT THE INVENTION

Figure 1:
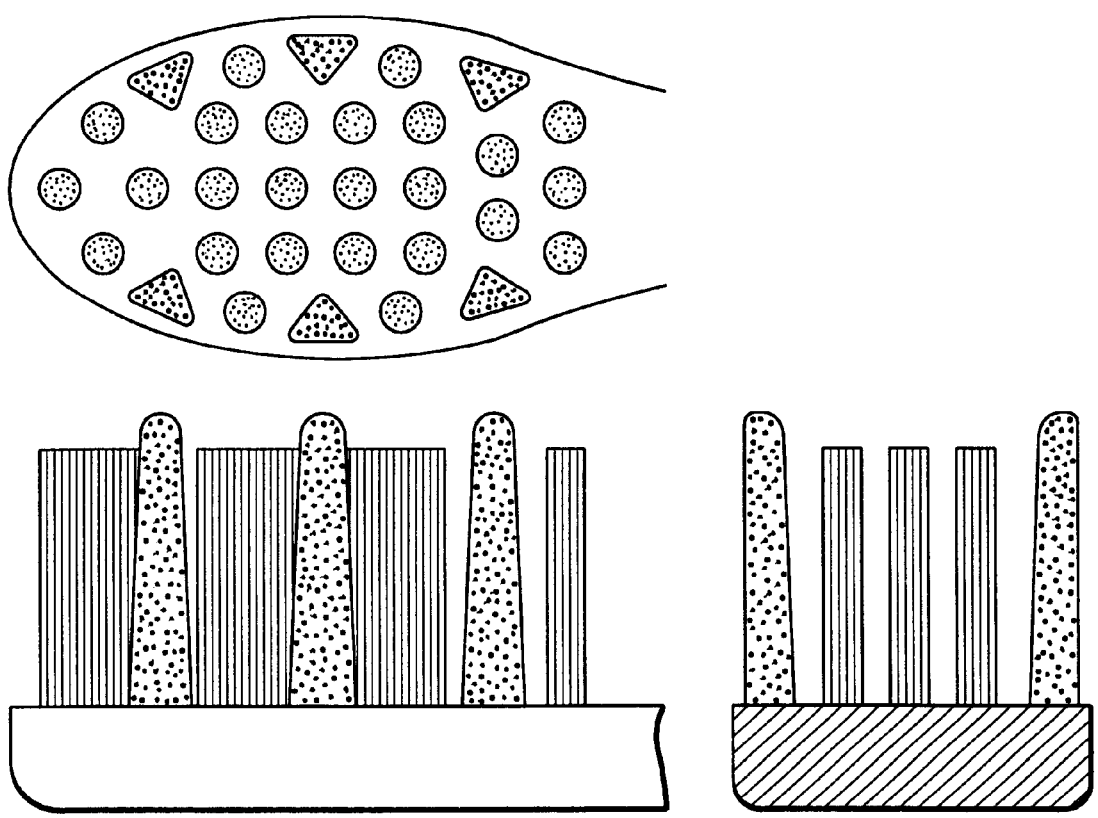
FIG. 1 illustrates a toothbrush provided with plaque removing bristles and gingiva-massaging portions in combination.

As the ingredient (A) employed in the present invention, illustrative of the pharmaceutically-active agent which acts on the periodontium are blood circulation stimulators, anti-inflammatory agents, hemostatic agents, analgesics, antihistamic agents, and plant extracts having effects of these agents.

Examples of the blood circulation stimulators can include vitamin E, dl-α-tocopherol nicotinate, and sodium chloride; and examples of the anti-inflammatory agents can include allantoin, β-glycyrrhetinic acid, glycyrrhetinic acid, epidihydro-cholesterol, dihydrocholesterol, ε-aminocapronic acid, hinokitiol, lysozyme chloride, indomethacin, and ibuprofen. Examples of the hemostatic agents can include tranexamic acid, thrombin, ascorbic acid, and rutin. Examples of the analgesics can include cimetidine, chlorpheniramine maleate, diphenhydramine hydrochloride, and promethazine hydrochloride. Examples of the plant extracts can include fennel extract, turmeric extract, scutellaria root extract, *Hypericum erectum* extract, chamomile extract, Sasa albo-marginata extract, Labiatae extract, sage extract, clove extract, ginseng extract, witch-hazel extract, fucus extract, horse chestnut extract, peach leave extract, rosemary extract, and eucalyptus extract.

On the other hand, examples of the microbicidal agent can include benzethonium chloride, chlorhexidine chloride, triclosan, cetylpyridinium chloride, isopropylmethylphenol, dequalinium chloride, and alkyldiaminoethylglycin hydrochloride.

These ingredients (A) can be used either singly or in combination, and preferably, can be added in a proportion of from 0.001 to 5 wt.%, notably from 0.01 to 1 wt.% based on the whole composition.

As the ingredient (B) employed in the present invention, the exothermic ingredient can be an exothermic substance which produces heat through a hydration reaction in the oral cavity. It is preferred to use the exothermic ingredient such that the resulting temperature reaches 38 to 50° C., especially 40 to 45° C. Specific examples of the exothermic ingredient can include anhydrous zeolite, anhydrous magnesium sulfate, sodium metaphosphate, calcium chloride, and dextrin.

Exothermic ingredients can be used either singly or in combination, and preferably, can be added in a proportion of from 5 to 50 wt.%, notably from 20 to 30 wt.% based on the whole composition.

On the other hand, examples of the water-soluble high-molecular substance as the ingredient (B) can include xanthan gum, dextrin, carageenan, hydroxypropylcellulose, and hydroxyethylcellulose. Of these, xanthan gum is most preferred when the water content is not higher than 5 wt.% as in the present invention.

These water-soluble high-molecular substances can be used either singly or in combination, and preferably, can be added in a proportion of from 0.1 to 2 wt.%, notably from 0.2 to 0.8 wt.%.

As the ingredient (B), one or more exothermic substances and one or more water-soluble high-molecular substances can be used in combination.

When an exothermic ingredient is used as the ingredient (B), thermal effects are available upon use. Massaging of gingivae with a composition for the oral cavity, said composition having such thermal effects, markedly improves the lymph function of the gingivae, so that the composition is useful for the prevention and/or treatment of paradental diseases. Further, use of a pharmaceutically-active agent, which acts on the periodontium, as the ingredient (A) makes it possible to correct the balance between a supply and a recovery of the interstitial fluid and hence, to promptly remedy and/or prevent paradental diseases, so that the resulting composition is more useful.

In addition, the use of the composition for the oral cavity, said composition having the thermal effects, hardly causes an ache and hence, permits comfortable brushing even when used by a hypersensitive person whose teeth are hurt by cold water.

The composition of this invention for the oral cavity has a water content not higher than 5 wt. %, preferably 3 wt. % or lower. Controlling of the water content at such a level can increase the adsorption rate of the pharmaceutically-active ingredient or the like on the oral mucosas and therefore, can heighten the effects for the prevention and/or treatment of paradental diseases.

An alkaline earth metal salt can be additionally incorporated in the composition of this invention for the oral cavity. It can reduce temperature-dependent variations of the viscosity of the composition. Described specifically, a paste or the like, the water content of which is low, becomes low in viscosity when exposed to high temperatures and, even after its temperature is allowed to drop to room temperature, is unable to regain its initial viscosity, so that the feeling of use may be impaired in some instances. When such an alkaline earth metal salt is added, the viscosity of the resulting composition does not drop but remains constant even after exposed to high temperatures.

The alkaline earth metal salt may be one of the exothermic substances exemplified above. Other examples can include magnesium salts such as magnesium chloride, magnesium hydroxide, magnesium lactate, magnesium oxide, magnesium nitrate, magnesium phosphate, and magnesium stearate; calcium salts such as calcium sulfate, calcium nitrate, calcium hydroxide, calcium gluconate, calcium pyrophosphate, calcium lactate, calcium metaphosphate, and calcium stearate; and barium salts such a barium chloride, barium nitrate, and barium stearate.

These alkaline earth metal salts can be used either singly or in combination, and for the stabilization of the viscosity, can preferably be added in a proportion of from 0.01 to 1 wt.%, especially from 0.05 to 0.8 wt.%, typically from 0.1 to 0.5 wt.% based on the whole composition.

To the composition of this invention for the oral cavity, glycerin, propylene glycol, polyethylene glycol, triglyceride, diglyceride, liquid paraffin or the like can be added as a liquid vehicle. These liquid vehicles can be used either singly or in combination and preferably, can be added in a proportion of from 30 to 80 wt.%, especially from 40 to 60 wt.% based on the whole composition.

Using one or more of these liquid vehicles, the composition of the present invention for the oral cavity may preferably be formulated into a use form such as gel, liquid, or paste.

Further, it is also possible to adjust the viscosity of the composition of this invention for the oral cavity by adding, in addition to the above-described water-soluble high-molecular substance, a thickener such as thickening silica (anhydrous silicic acid) or the like as needed.

It is preferred to use one or more of such thickeners to adjust the Helical-path viscosity of the composition at 25° C. such that it falls within 3,000 to 15,000 dPa·s, especially 4,000 to 10,000 dPa·s. Incidentally, "Helical-path viscosity" as used herein means a value measured by using a "B8R-type Viscometer" equipped with a helical stand controller (rotor E, rotational speed: 2.5 r/min, measured: for 1 minute).

To the composition of this invention for the oral cavity, ingredients commonly employed in compositions for the oral cavity, for example, surfactants, abrasives, sweeteners, flavoring agents, preservatives, whitening agents, humectants, binders and the like can be added as needed to extents not impairing the effects of the present invention.

The composition of this invention for the oral cavity can be produced in a manner known per se in the art.

The composition of this invention for the oral cavity permits adsorption of a pharmaceutically-active ingredient or the like at a high rate on the oral mucosas, and is excellent in the effects of preventing and/or treating paradental diseases. The composition according to the present invention, therefore, is useful as a periodentium, especially gingiva care composition and also as a dentifrice composition, especially a toothpaste composition.

The composition according to the present invention may preferably be used by applying it into the oral cavity and brushing the teeth and/or gingivae. For such brushing, use of a toothbrush provided with plaque removing bristles and gingiva-massaging portions in combination is especially preferred, although a conventional toothbrush, namely, a toothbrush having plaque removing bristles or a toothbrush having massaging portions may also be used. Usable as these toothbrushes are those disclosed, for example, in JP 5-228019 A, JUM 47-1378 A, JUM 62-35527 A, JUM 6-31940 B and JUM 6-12647 B.

Specific usable examples can include those having rubbery bristles implanted or bonded on an outer edge portion of an inner wall of a block head and those having tufts and/or rubbery rod-like bristles implanted aslant on an outer edge portion of an inner wall of a block head such that the tufts and/or rubbery rod-like bristles extend in outward directions.

Among these, a toothbrush—which is provided, at at least longitudinal edge portions of an inner wall of a block head thereof, with portions where plural types of tufts different in the modulus of elasticity and length or rubbery rod-like bristles extend aslant in outward directions (see FIG. 1)—is suitable because it allows to efficiently massage the margins and papillae of the gingivae at the same time.

Concerning the different moduli of elasticity, it is preferred, for example, to implant two or more kinds of bristles or rubbery rod-like bristles different in the modulus of elasticity when only bristle tufts or rubbery rod-like bristles are used or to implant bristle tufts and rubbery rod-like bristles, which are different in the modulus of elasticity, together when bristles and rubbery rod-like bristles are used in combination. The different lengths, on the other hand, may comprise two or more lengths. It is preferred to make those having a higher modulus of elasticity longer than those having a lower modulus of elasticity. The difference between the longer length and the shorter length may preferably range from 0.5 to 3.0 mm or so. Further, the rubbery rod-like bristles may preferably have, as a transverse cross-sectional shape thereof, a substantially triangular shape with a longest side thereof directed outwards.

When brushing is performed in a usual manner by using the composition of the present invention and the above-described toothbrush, the teeth and gingivae can be brushed at the same time, thereby making it possible to effectively perform removal of plaque and massaging of the gingivae at the same time.

EXAMPLES

Example 1

Dentifrices of the formulations shown in Table 1 were prepared in a manner known per se in the art.

Each of the thus-obtained dentifrices had high adsorption rates of the pharmaceutically-active agents on the oral mucosas and was excellent in the effects of preventing and/or treating paradental diseases. With Invention Products 1–3, thermal effects were also obtained, bringing about superior effects.

TABLE 1

| Ingredient | Invention product | | | |
|---|---|---|---|---|
| (parts by weight) | 1 | 2 | 3 | 4 |
| dl-α-Tocopherol acetate | 0.10 | | | 0.10 |
| dl-α-Tocopherol nicotinate | | | 0.05 | |
| β-Glycyrrhetinic acid | 0.01 | | | |
| Allantoin | | 0.01 | | |
| Triclosan | | | 0.01 | |
| Benzethonium chloride | 0.01 | | | 0.01 |
| Cetylpyridinium chloride | | 0.01 | | |
| Anhydrous zeolite | 20.0 | 45.0 | 30.0 | |
| Magnesium sulfate | 5.0 | | | |
| Xanthan gum | 0.50 | | 0.80 | |
| Hydroxypropylcellulose | | 0.50 | | |
| Carageenan | | | | 0.40 |
| Calcium hydrogenphosphate | 10.0 | | | |
| Calcium carbonate | | | 20.0 | 20.0 |
| Glycerin | 32.0 | 51.33 | 37.0 | 30.46 |
| Propylene glycol | 25.18 | | | 29.0 |
| Polyethylene glycol 600 | | | 10.0 | |
| Anhydrous silicic acid | 5.0 | | | 12.0 |
| Sodium laurylsulfate | 1.0 | 1.0 | 0.50 | 1.10 |
| Sodium monofluorophosphate | | 0.76 | | 0.68 |
| Paraoxybezoate ester | | 0.10 | 0.10 | 0.10 |
| Saccharin sodium | 0.20 | 0.20 | 0.20 | 0.15 |
| Flavoring agent | 1.0 | 1.0 | 1.0 | 1.0 |
| Purified water | | q.s. | q.s. | q.s. |
| Total | 100 | 100 | 100 | 100 |
| Helical-path viscosity (25° C.; dPa·s) | 4800 | 14200 | 6800 | 13500 |

Example 2

A dental cream of the formulation shown below was prepared in a manner known per se in the art (helical-path viscosity at 25° C.: 14,800 dPa·s).

The thus-obtained dental cream was suited for massaging the gingivae, and excellent effects were obtained for the prevention and treatment of paradental diseases.

TABLE 2

| (Ingredient) | (wt. %) |
|---|---|
| Cetylpyridinium chloride | 0.01 |
| β-Glycyrrhetinic acid | 0.01 |
| Triglyceride | 27.85 |
| Liquid paraffin | 25.93 |
| Xanthan gum | 0.20 |
| Dextrin | 35.00 |
| Anhydrous silica | 10.00 |
| Flavoring agent | 1.00 |
| Total | 100.00 |

Test 1 (Water Content, and Remaining Amount of Pharmaceutically-active Agent)

Paste A of the formulation shown in Table 3, which contained 0.1% of vitamin E and was controlled at about 5 wt.% in water content, and Paste B of the formulation presented in Table 3, which contained 0.1% of vitamin E and was controlled at about 10 wt.% in water content, were separately dispersed to a concentration of 1.0 g/mL in artificial saliva. After each paste solution was centrifuged, 1 g of the resultant supernatant was added to 0.5 g of oral mucosa cells sampled by the method reported by N. R. Badcock et al. in J. Chromatography, 328, 290–296 (1986). The mixture so obtained was stirred and then left standstill under incubation at 37° C. After the treated oral mucosa cells of each test sample were washed with deionized water, vitamin E still remaining in the oral mucosa cells was extracted in methanol by ultrasonic disruption, and the extracted vitamin E was quantitated by high-performance liquid chromatography.

As a result, the amount of vitamin E remaining in the oral mucosa cells after the treatment of Paste A was found to be three times as much as that of vitamin E remaining after the treatment of Paste B.

TABLE 3

| Ingredient (wt. %) | Paste A | Paste B |
|---|---|---|
| Vitamin E | 0.1 | 0.1 |
| Propylene glycol | 53.4 | 48.2 |
| Xanthan gum | 0.5 | 0.5 |
| Sodium laurylsulfate | 1.0 | 1.0 |
| Anhydrous silicic acid | 12.0 | 12.0 |
| Calcium hydrogenphosphate | 30.0 | 30.0 |
| Purified water | 3.0 | 8.2 |
| Total | 100 | 100 |
| Helical-pass viscosity (25° C.; dPa·s) | 7840 | 16000 |

Test 2 (Remaining Amount of Pharmaceutically-active Agent upon Addition of Exothermic Ingredient)

Pastes C–F, to which 0.1% of vitamin E had been added and an exothermic ingredient had also been added (water content: about 3 wt.%), were separately dispersed to a concentration of 1.0 g/mL in artificial saliva of 37° C., immediately followed by the measurement of the temperatures of the thus-dispersed solutions. After each paste solution was centrifuged, its supernatant was caused to react with oral mucosa cells in a similar manner as in Test 1, and the reaction mixture was left standstill for 3 minutes at the above-measured temperature of the corresponding dispersed solution. Vitamin E still remaining in the oral mucosa cells was quantitated as in Test 1.

As a result, it was found that compared with Paste C to which the exothermic ingredient was not added, the remaining amount of vitamin E was 1.2 times as much in the case of Paste D the temperature of which reached 38° C., 1.8 times as much in the case of Paste E the temperature of which reached 40° C., and 2 times as much in the case of Paste F the temperature of which reached 50° C.

TABLE 4

| Ingredient (wt. %) | Paste C | Paste D | Paste E | Paste F |
|---|---|---|---|---|
| Vitamin E | 0.1 | 0.1 | 0.1 | 0.1 |
| Propylene glycol | 72.4 | 72.4 | 72.4 | 72.4 |
| Xanthan gum | 0.5 | 0.5 | 0.5 | 0.5 |
| Sodium laurylsultate | 1.0 | 1.0 | 1.0 | 1.0 |
| Anhydrous silicic acid | 6.0 | 6.0 | 6.0 | 6.0 |
| Sodium hydrogenphosphate | 20.0 | — | — | — |
| Sodium metaphosphate | — | 20.0 | — | — |
| Anhydrous zeolite | — | — | 20.0 | — |
| Anhydrous magnesium sulfate | — | — | — | 20.0 |
| Total | 100 | 100 | 100 | 100 |
| Helical-pass viscosity (25° C.; dPa·s) | 2800 | 5700 | 4800 | 6000 |
| Temperature* | 25° C. | 25° C. | 25° C. | 25° C. |

*Temperature of each paste after stirring subsequent to the addition of an equiamount of artificial saliva (37° C.).

Example 3

Dentifrices (pastes) of the formulations shown in Table 5 were prepared in a manner known per se in the art.

Each of the thus-obtained dentifrices had high adsorption rates of the pharmaceutically-active agents on the oral mucosas and was excellent in the effects of preventing and/or treating paradental diseases.

With respect to the dentifrices so obtained, temperature cycling storage at 25° C.–50° C.–25° C. (at each of which the dentifrices were stored for 24) was conducted, and the viscosities of the dentifrices were measured by helical-pass viscometer both before and after the storage. As a result, it was found that after the storage, each of the pastes was free of a drop in the viscosity and its viscosity remained constant.

TABLE 5

| Ingredient (parts by weight) | Invention product | | | |
|---|---|---|---|---|
| | 5 | 6 | 7 | 8 |
| dl-α-Tocopherol acetate | 0.10 | | | 0.10 |
| dl-α-Tocopherol nicotinate | | 0.05 | | |
| β-Glycyrrhetinic acid | 0.01 | | | |
| Triclosan | | | 0.01 | |
| Benzethonium chloride | 0.01 | | | 0.01 |
| Cetylpyridinium chloride | | 0.01 | | |
| Anhydrous zeolite | | | 30.0 | 20.00 |
| Magnesium sulfate | 0.50 | | | |
| Xanthan gum | 0.50 | | 0.50 | |
| Hydroxypropylcellulose | | 0.50 | | |
| Carageenan | | | | 0.40 |
| Calcium sulfate | | | 0.20 | |
| Barium sulfate | | | 0.20 | |
| Calcium hydrogenphosphate | 18.0 | | | |
| Magnesium hydroxide | | | 0.10 | |
| Calcium carbonate | | | | 20.0 |
| Calcium gluconate | | | | 0.70 |
| Glycerin | 40.00 | 46.03 | 37.54 | 33.36 |
| Propylene glycol | 28.59 | 20.0 | | 30.0 |
| Polyethylene glycol 600 | | | 10.0 | |
| Anhydrous silicic acid | 10.0 | | | 12.0 |
| Aluminum hydroxide | | | 30.0 | |
| Sodium laurylsulfate | 1.0 | 1.0 | 0.50 | 1.10 |
| Sodium monofluorophosphate | | 0.76 | | 0.68 |
| Paraoxybezoate ester | | 0.10 | 0.10 | |
| Saccharin sodium | 0.20 | 0.20 | 0.20 | 0.15 |
| Flavoring agent | 1.00 | 1.00 | 1.00 | 1.00 |
| Purified water | | | | q.s. |
| Total | 100 | 100 | 100 | 100 |
| Helical-path viscosity (25° C.; dPa · s) | 10000 | 10400 | 13800 | 12000 |

Example 5

Using the dentifrices of Invention Products 1 and 2 in Table 1, those suffering from light inflammation at their gingivae brushed their teeth with toothbrushes each of which was provided with plaque-removing bristles and gingiva-massaging portions as shown in FIG. 1. Compared with brushing the teeth with conventional toothbrushes, a higher effect was observed in improving the inflammation of the gingivae.

Industrial Applicability

The compositions of the present invention for the cavity permit adsorption of a pharmaceutically-active agent or a microbicidal agent at a high rate on the oral mucosas and are excellent in the effects of preventing and/or treating paradental diseases.

What is claimed is:

1. A composition for the oral cavity, comprising
   (A) a pharmaceutically-active agent, which acts on the periodontium, or a microbicidal agent,
   (B) 20–50 wt. % of an exothermic ingredient,
   (C) 0.1–2 wt. % of a water-soluble polymeric substance, and
   (D) an alkaline earth metal salt,
   wherein said composition has a water content not higher than 5 wt. %,
   said pharmaceutically-active agent or said microbicidal agent is present in an amount effective for preventing and/or treating paradental disease and an amount which is less than an amount used for preventing and/or treating paradental disease in the absence of said exothermic ingredient, and
   wt. % is based on a total weight of said composition.

2. A composition for the oral cavity according to claim 1, wherein said composition has a helical-path viscosity at 25° C. of from 3,000 to 15,000 dPa·s.

3. A composition for the oral cavity according to claim 1, which is a periodontium care composition.

4. A composition for the oral cavity according to claim 1, which is a dentifrice composition.

5. An intraoral treatment method, which comprises brushing the teeth and/or gingivae with a composition for the oral cavity according to claim 1.

6. A method according to claim 5, wherein said brushing is performed by a toothbrush provided with plaque removing bristles and gingiva-massaging portions in combination.

7. The composition for the oral cavity according to claim 1, wherein the pharmaceutically active agent is selected from the group consisting of blood circulation stimulators, anti-inflammatory agents, hemostatic agents, analgesics, antihistamine agents, plant extracts exhibiting blood circulation stimulation activity, plant extracts exhibiting anti-inflammatory activity, plant extracts exhibiting hemostatic activity, plant extracts exhibiting analgesic activity, plant extracts exhibiting antihistamine activity and plant extracts exhibiting anti-inflammatory activity.

8. The composition for the oral cavity according to claim 1, wherein the microbicidal agent is selected from the group consisting of benzethonium chloride, chlorhexidine chloride, triclosan, cetylpyridinium chloride, isopropylmethylphenol, dequalium chloride and alkyldiaminoethylglycine hydrochloride.

9. The composition for the oral cavity according to claim 1, wherein the exothermic ingredient is selected from the group consisting of anhydrous zeolite, anhydrous magnesium sulfate, sodium metaphosphate, calcium chloride, dextrin and mixtures thereof.

10. The composition for the oral cavity according to claim 1, wherein the alkaline earth metal salt is selected from the group consisting of magnesium chloride, magnesium hydroxide, magnesium lactate, magnesium oxide, magnesium nitrate, magnesium phosphate, magnesium stearate, calcium sulfate, calcium nitrate, calcium hydroxide, calcium gluconate, calcium pyrophosphate, calcium lactate, calcium metaphosphate, calcium stearate, barium chloride, barium nitrate and barium stearate.

11. The composition for the oral cavity according to claim 1, wherein the alkaline earth metal salt is the same as the exothermic ingredient.

12. The composition for the oral cavity according to claim 1, wherein the alkaline earth metal salt is from 0.05 to 0.08 wt. %.

13. The composition for the oral cavity according to claim 1, wherein a helical path viscosity of the composition is from 4,000 to 10,000 dPa·s.

14. The composition for the oral cavity according to claim 1, wherein the water-soluble polymeric substance is selected from the group consisting of xanthan gum, dextrin, carageenan, hydroxypropylcellulose, hydroxyethylcellulose and mixtures thereof.

15. The method as claimed in claim 5, wherein the temperature of the intraoral cavity reaches from 38 to 50° C.

* * * * *